United States Patent [19]

Rosenberg

[11] Patent Number: 4,553,537

[45] Date of Patent: Nov. 19, 1985

[54] SURGICAL BARRIER

[76] Inventor: Max Rosenberg, 1721 Nashville Ave., New Orleans, La. 70115

[21] Appl. No.: 502,729

[22] Filed: Jun. 9, 1983

[51] Int. Cl.⁴ .............................................. A61F 13/00
[52] U.S. Cl. .................................. 128/132 R; 128/156
[58] Field of Search ................... 128/132 R, 155, 156, 128/157, 132 D; 604/358

[56] References Cited

U.S. PATENT DOCUMENTS 3,372,696  3/1968  Rudie .............................. 128/132 R
3,934,582  1/1976  Gorrie ............................ 128/132 D Primary Examiner—John D. Yasko
Attorney, Agent, or Firm—Cushman, Darby & Cushman

[57] ABSTRACT

A knitted tubular fabric is made from a synthetic yarn having a low capacity for liquid absorption; the ends of the tubular fabric are stitched closely so that the fabric will lie flat; the fabric is elongated in shape compared to its width and is used to provide a barrier around the edge of a surgical site, particularly in the abdomen, to be held in place by hand or by mechanical retractors to hold back away from the site other internal organs; the interior of the tubular fabric may be provided with a thin flexible liquid impervious sheet and which is held in place by parallel stitching along the length of the fabric.

15 Claims, 3 Drawing Figures

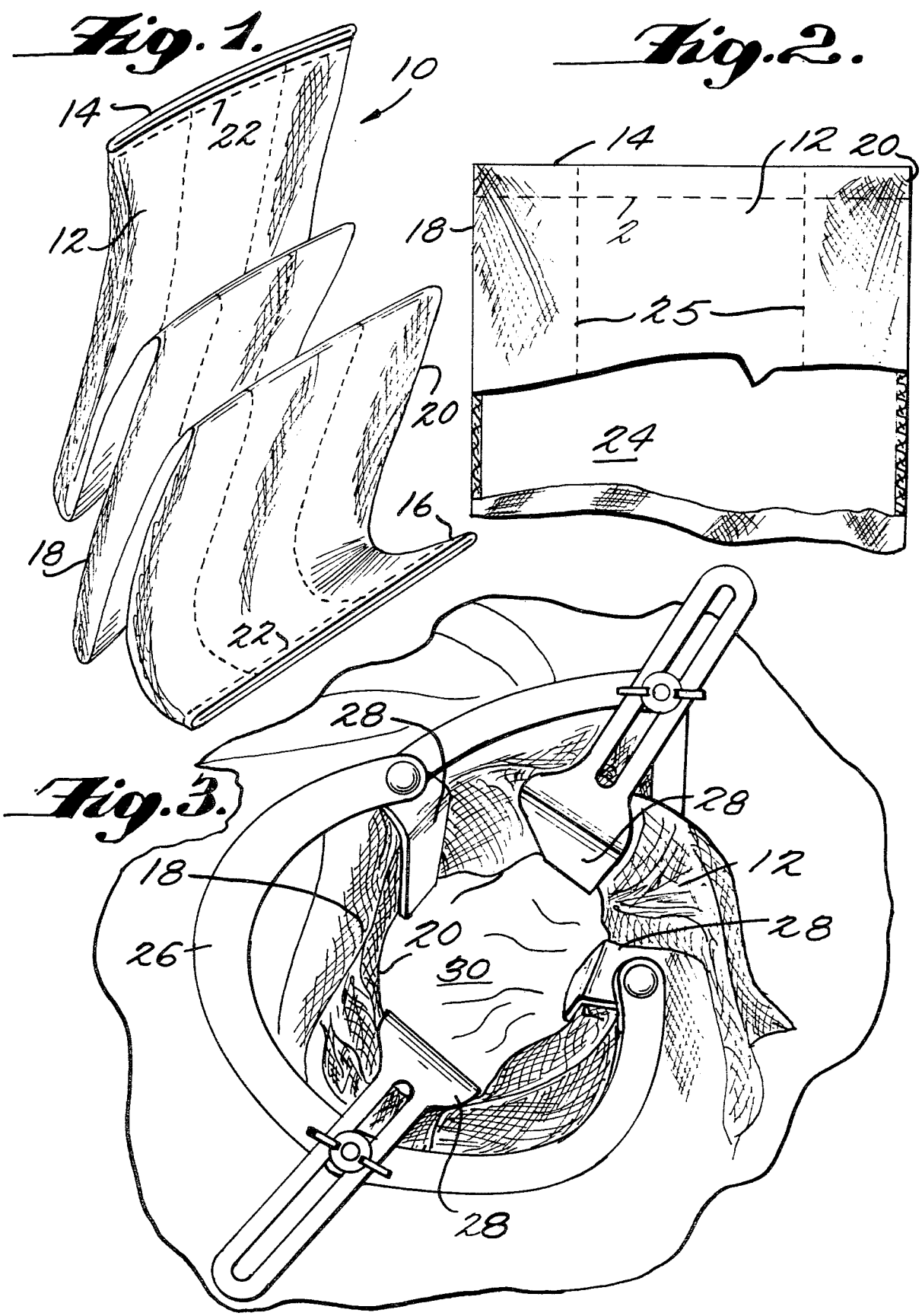

SURGICAL BARRIER

BACKGROUND OF THE INVENTION

The present invention relates to a textile fabric designed to control the position of adjacent internal organs about an operation site during a surgical operation.

It is absolutely necessary that a surgeon have good exposure of the organ system needing surgery in order to execute the surgical procedure. The conventional technique employed to provide surgical exposure includes the use of metal retractors, either self-retaining or hand held, or both, or by the sterile gloved hand of an assistant. To minimize trauma to body tissue, these instruments are used in conjunction with highly absorbent cotton laparotomy sponge pads or lengths of cotton gauze dressing or bandages.

Soft cotton laparotomy sponge pads were designed for the purpose of acting as sponges to be used to absorb serum and blood exuded during the operative procedure in order to keep the surgical field free of these and other body fluids. Lengths of cotton gauze bandage, on the other hand, were designed to be used as surgical dressings for wound cover. They are used to minimize bacterial contamination of a wound, to compress the wound so as to restrict leakage of body fluid and to absorb those fluids from the wound whose escape cannot be prevented.

The use of absorbent cotton laparotomy sponge pads and absorbent cotton gauze dressings for the purpose of securing surgical exposure represents a serious and disadvantageous application and is responsible for poor exposure of the site with frequent complications. Cotton fiber material has been considered the traditionally safe material for use in the peritoneal cavity. However, within recent years it has become apparent that cotton products give off an extraordinary amount of irritating cotton lint which can react intensely with abdominal viscera and peritoneal surfaces. The reactions to cotton fiber lint has been the cause of frequent occurrences of intraperitoneal inflammatory reaction noted post operatively (see Miller, *American Journal of Surgery*, February, 1980, page 295, *Annals of Surgery*, January, 1967, Sturdy, et al).

Using absorbent cotton products as devices to hold intestine or other viscera in special positions is also inappropriate. When the absorbent cotton products are placed into the peritoneal cavity, they absorb large quantities of body fluids. The fluids cause the cotton fibers to swell and soften and the overall firmness of the dry material is lost so that the fabric looses its ability to hold back peritoneal viscera which then fall onto the operative field. In order to be able to continue with the surgical procedure, repeated introduction of increasing numbers of cotton laparotomy pads becomes necessary to shore up the support function of the initially introduced pads that are no longer effective.

The introduction of multiple laparotomy sponge pads as well as other objects into the peritoneal cavity sets the stage for very serious and not uncommon complications should one or more objects placed in the peritoneal cavity slip away from visual accountability. Objects lost in this manner have been inadvertently left to remain in the peritoneal cavity after the abdominal surgery was completed. This has resulted in the most serious of surgical complications as well as death (see *Annals of Surgery*, January, 1967, Sturdy, et al).

SUMMARY OF THE INVENTION

The present invention relates to a textile fabric constructed of synthetic fiber in a manner that enables it to be safely placed into the major body cavities in contact with various internal organs thereby holding them in special positions which prevents them from obstructing the operative field and the progress of a surgical procedure.

It is the object of the invention to construct a fabric device that is soft and malleable, whose knit or weave and fiber quality form a fabric whose density and compactibility will provide good barrier support of internal organs, at the same time being resilient, and atraumatic to the intraperitoneal structures even though these structures may be held in restricted positions for extended periods of time.

It is also the object of this invention to construct this woven or knitted fabric of fiber materials which do not cause tissue inflammatory reactions on contact with the tissues of intraperitoneal structures in spite of prolonged contact with these tissues.

An additional objective of the invention is to construct the woven surgical barrier of synthetic fiber material which does not absorb liquid into the fiber structure and therefore will not result in softening of the fabric and loss of the surgical barrier support no matter how great the quantity of body fluid encountered in the body cavity nor how long the fluids remain in contact with the barrier fabric.

Another objective is to construct the synthetic woven fabric into an elongated tubular form which eliminates the need to stitch long lengths of raw edges while preserving the elongated, malleable shape that permits the fabric device although uniquely long to be easily introduced into most body activities, especially in any area of the peritoneal cavity, in such a manner that the fabric of this invention placed against intraperitoneal organs will not only prevent unwanted structures such as the intestine from falling into the operative field, but additionally creates a surgical amphitheatre, as it were, in which the surgeon can operate. By producing a defined surgical area the invention not only permits unrestricted surgical action, the present invention minimizes the possibility that sponges and instruments might be left inside the patient and because of its design as a single unit of its size, it represents a unique unlosable surgical device.

The foregoing and other advantages will become apparent as consideration is given to the following detailed description taken in conjunction with the accompanying drawings, in which:

BRIEF DESCRIPTION OF THE DRAWINGS

FIG. 1 is a perspective view of the surgical barrier of the present invention;

FIG. 2 is a top plan view of one end with parts broken away; and

FIG. 3 is a perspective view of the surgical site with the surgical barrier of the present invention in place.

DETAILED DESCRIPTION OF THE INVENTION

Turning now to the drawings wherein like numerals designate corresponding parts throughout the several views, there is shown in FIG. 1 a surgical barrier or wall 10 of the present invention. In the illustrated embodiment, the surgical barrier 10 comprises a knitted tube 12 having opposite ends 14 and 16 and side edges 16 and 18 extending along the length dimension of the tube 12. The ends 14 and 16 are closed by a transverse stitch line 22 which is inserted after the free ends are folded inwardly whereby the stitching will prevent any unravelling and will assure that the ends 14 and 16 remain smooth.

The tube 12 may be knitted on a conventional circular knitted machine and the same knitting pattern as is used in stretch hosiery may be employed. Typically, a length of about seven feet and a width of six inches should be sufficient for most applications.

While cotton yarn may be employed to form the tube 12, in the preferred embodiment, a synthetic fiber such as polyester, polypropylene or polyethylene, or even acrylic fibers should be used as such synthetic fibers release a very low level of lint material as compared to cotton and their ability to absorb fluids is greatly reduced as compared to cotton.

To further enhance the water repellancy of the tube 12, the outer surface of the tube may be coated with a water repellant liquid such as a latex coating marketed under the name Seran by Dow Chemical Company, the Surlyn Ionomer Dispersions manufactured by DuPont Chemicals or a silicon coating.

In the alternative, or to further reduce liquid absorption and to positively prevent any liquids outside of the barrier when placed around a surgical site from passing through the barrier, a liquid imprevious sheet 24 may be inserted in the tube along its length and held in place by the two rows of stitches 25 which extend through the fabric as well as through the sheet 24 located interiorly of the tube. It will be noted that the two parallel rows of stitches 25 are spaced inwardly from the edges 18 and 20 of the tube 12. With this arrangement, the insertion of the tube 12 into a surgical site is facilitated since the edge portions 18 and 20 remain highly flexible. The stitching 22 at each end of the tube and at 25 will also assure that the liquid impervious sheet 24 remains in place in the fabric. The sheet 24 may be thin polypropylene, polyethylene or polyester sheet.

In use, a surgeon will first make an incision and as soon as the surgical site is reached, retractors 26 may be put in place and then the tube 12 which will assume the flat condition illustrated in FIG. 1 by virtue of the stitchings 22 is inserted into the site behind the arms 28 of the retractor 26. Any excess length may be simply draped over one of the retractor arms 26. Due to its unique construction, the tube 12 will not collapse as has been the case with cotton pads that have previously been used. It will also be evident that the surgical barrier 10 may be held in place during an operation by the hands of an assistant as well.

The elongated shape and malleability of the barrier 10 of this invention permits the surgeon to easily fold the flat tube 12 into the abdominal cavity and place it in contact with the displaced viscera. The introduction of the flat tube 12 continues until a soft, resilient buttress 10 is created which gently presses against and maintains the desired position of potentially interfering structures away from the operative field, preventing them from interfering with the operation. The deployment of the tube 12 is continued in such a manner as to fashion a wall 10 extending from one abdominal border to the other, the present invention being such that it can accommodate to any body cavity size or consistency. After the "reatining" wall 10 is created the support section of the self-retaining retractor 28 or a hand-held retractor is placed in position over the invention, the operative field is ready for the surgical procedure to begin. If at any time during the operation there is a temporary lessening of anesthesia and therefore an increase in intra-abdominal pressure, the resistance of the present invention harmlessly prevents the walled off viscera from entering the surgical field.

Since the invention is constructed of synthetic fiber, any fluid that is encountered within the peritoneal cavity does not cause a softening or collapse of the reatining wall as would occur if cotton sponge pads or gauze were used. Furthermore, when multiple cotton sponge pads are used in this way, becoming soaked with body fluids and discolored, they are easily overlooked and have often slipped between folds of intestine or behind larger abdominal structures only to be left behind to cause serious complications. The fabric amphitheater created by the present invention not only minimizes the loss of multiple cotton sponges and instruments, but tends to minimize dissemination of noxious fluid and other matter away from the operative site.

At the completion of the surgical procedure, all instruments and sponges are removed and placed for counting. Because of the containment action of the invention the appropriate use of laparotomy sponge pads and instruments is made more safe.

It will be obvious to those skilled in the art that the invention not only more effectively provides surgical exposure, it also renderes the use of laparotomy pads more safe as well as having other advantages.

One of the frequent problems in surgery results from leaving small articles such as sponges in the incision after completing the operation. As will be evident from the foregoing, the surgical barrier of the present invention provides a very well-defined area which will prevent such objects from slipping away from the physician into other cavities adjacent to the site of the operation.

Having described the invention, it will be apparent to those skilled in this art that various modifications may be made thereto without departing from the spirit and scope of this invention as defined in the appended claims.

What is claimed is:

1. A woven structure for use in a surgical operation comprising an elongate, tubular knit fabric having opposite ends, means closing said ends so that said fabric will be flattened and malleable and conformable to internal body cavities, said structure including means for reducing absorption of liquids by the fabric, said fabric having a selected width and length and said means for reducing absorption of liquids comprising a thin sheet of liquid impervious material disposed within said tubular fabric, said sheet having substantially the same width and length as said fabric, means securing said sheet in place within said fabric.

2. The invention as claimed in claim 1 wherein said securing means comprises stitching extending through said fabric and said sheet.

3. The invention as claimed in claim 1 wherein said sheet is a polypropylene film.

4. The invention as claimed in claim 1 wherein said sheet is a polyethylene film.

5. The invention as claimed in claim 1 wherein said sheet is a polyester film.

6. A woven structure for use in a surgical operation comprising an elongate, tubular knit fabric having opposite ends, means closing said ends so that said fabric will be flattened and malleable and conformable to internal body cavities, said structure including means for reducing absorption of liquids by the fabric, said means for reducing absorption of liquids comprising a silicon coating applied to the surface of said fabric.

7. The invention as claimed in claim 1 wherein said fabric is knitted from a synthetic yarn.

8. The invention as claimed in claim 1 wherein said yarn is polyethylene.

9. The invention as claimed in claim 1 wherein said yarn is polyester.

10. The invention as claimed in claim 7 wherein said means closing each said end comprises stitching extending transverse to each said end.

11. The method of performing surgical operations in the abdomen comprising the steps of:
   making an incision to provide access to the operation site;
   inserting into the incision a flexible barrier structure comprising an elongate, tubular fabric including means for reducing absorption of liquids;
   placing said fabric around the periphery of the operation site in the incision; and
   holding the fabric in its surrounding position during the operation.

12. The invention as claimed in claim 11 including the step of using retractor means for holding the fabric in its surrounding position.

13. The invention as claimed in claim 6 wherein said fabric is knitted from a synthetic yarn.

14. The invention as claimed in claim 1 wherein said securing means comprises stitching extending through said fabric and said sheet, said stitching including two lines of stitches extending in substantially parallel relation from one end of said fabric to the other end along the length dimension of said fabric, each said line being spaced apart from one another and spaced apart from the edges of said fabric.

15. A woven structure for use in a surgical operation comprising an elongate, tubular knit fabric having opposite ends, means closing said ends so that said fabric will be flattened and malleable and conformable to internal body cavities, said structure including means for reducing absorption of liquids by the fabric, said means for reducing absorption of liquids including a thin sheet of liquid impervious material disposed within said tubular fabric, said fabric having stitching extending through said fabric and said thin sheet to hold said sheet in place within said fabric.

* * * * *